(12) United States Patent
Cowin et al.

(10) Patent No.: US 11,944,508 B1
(45) Date of Patent: Apr. 2, 2024

(54) AUGMENTED REALITY SURGICAL ASSISTANCE SYSTEM

(71) Applicant: Altair Innovations, LLC, Lake Mary, FL (US)

(72) Inventors: David J. Cowin, Orlando, FL (US); Chetan K. Patel, Lake Mary, FL (US)

(73) Assignee: Altair Innovations, LLC, Lake Mary, FL (US)

( * ) Notice: Subject to any disclaimer, the term of this patent is extended or adjusted under 35 U.S.C. 154(b) by 0 days.

(21) Appl. No.: 17/574,646

(22) Filed: Jan. 13, 2022

(51) Int. Cl.
| | |
|---|---|
| *A61B 90/00* | (2016.01) |
| *A61B 6/00* | (2006.01) |
| *A61B 6/46* | (2024.01) |
| *G02B 27/01* | (2006.01) |
| *G06T 7/00* | (2017.01) |
| *G06T 7/62* | (2017.01) |
| *G06T 7/70* | (2017.01) |
| *G06T 11/00* | (2006.01) |

(52) U.S. Cl.
CPC .............. *A61B 90/37* (2016.02); *A61B 6/463* (2013.01); *A61B 6/487* (2013.01); *A61B 6/56* (2013.01); *G02B 27/0172* (2013.01); *G06T 7/0012* (2013.01); *G06T 7/62* (2017.01); *G06T 7/70* (2017.01); *G06T 11/00* (2013.01); *A61B 2090/3616* (2016.02); *A61B 2090/365* (2016.02); *A61B 2090/376* (2016.02); *G02B 2027/014* (2013.01); *G02B 2027/0178* (2013.01); *G06T 2207/10016* (2013.01); *G06T 2207/10121* (2013.01); *G06T 2207/30004* (2013.01)

(58) Field of Classification Search
CPC ......... A61B 90/37; A61B 6/463; A61B 6/487; A61B 6/56; A61B 2090/3616; A61B 2090/365; A61B 2090/376; G06T 7/62; G06T 7/70; G06T 7/0012; G06T 11/00; G06T 2207/10016; G06T 2207/10121; G06T 2207/30004; G02B 27/0172; G02B 2027/014; G02B 2027/0178
USPC ........................................................ 345/109
See application file for complete search history.

(56) References Cited

U.S. PATENT DOCUMENTS

| | | | |
|---|---|---|---|
| 7,627,334 | B2 | 12/2009 | Cohen et al. |
| 8,075,627 | B2 | 12/2011 | Caylor, III et al. |
| 8,108,036 | B2 | 1/2012 | Tran |
| 8,566,115 | B2 | 10/2013 | Moore |
| 9,254,086 | B2 | 2/2016 | Vink et al. |
| 9,310,613 | B2 | 4/2016 | Jacobsen et al. |
| 9,344,686 | B2 | 5/2016 | Moharir |
| 9,452,023 | B2 | 9/2016 | Boillot et al. |

(Continued)

FOREIGN PATENT DOCUMENTS

| | | |
|---|---|---|
| CN | 110602459 A | 12/2019 |
| WO | 2008/146207 A2 | 12/2008 |

(Continued)

*Primary Examiner* — Mark Edwards
(74) *Attorney, Agent, or Firm* — Jones Walker LLP

(57) ABSTRACT

A medical video processing system (MVPS) including a system housing and electronic circuitry within the housing. The electronic circuitry is configured to (a) receive medical video imagery; (b) process the medical video imagery in order to superimpose a virtual medical object (VMO) on the medical video imagery; and (c) transmit the medical video imagery with the VMO in a format that may be received on a wireless display.

12 Claims, 13 Drawing Sheets

(56) References Cited

U.S. PATENT DOCUMENTS

| | | |
|---|---|---|
| 9,544,533 B2 | 1/2017 | Priest |
| 9,788,907 B1 | 10/2017 | Alvi et al. |
| 9,861,446 B2 | 1/2018 | Lang |
| 2002/0055918 A1 | 5/2002 | Hlathein et al. |
| 2004/0024288 A1 | 2/2004 | Uchikubo |
| 2008/0004904 A1 | 1/2008 | Tran |
| 2008/0178090 A1 | 7/2008 | Mahajan et al. |
| 2008/0221399 A1 | 9/2008 | Zhou et al. |
| 2008/0319275 A1 | 12/2008 | Chiu et al. |
| 2009/0179985 A1 | 7/2009 | Amling |
| 2009/0300507 A1 | 12/2009 | Raghavan et al. |
| 2011/0221669 A1 | 9/2011 | Shams et al. |
| 2012/0316502 A1* | 12/2012 | Mehdizade ........ A61B 1/00073 604/164.01 |
| 2013/0238702 A1 | 9/2013 | Sheth et al. |
| 2014/0006943 A1 | 1/2014 | Robbins et al. |
| 2014/0031668 A1 | 1/2014 | Mobasser et al. |
| 2014/0043026 A1* | 2/2014 | Frahm .................... G01R 33/48 324/309 |
| 2014/0164968 A1 | 6/2014 | Aalami |
| 2014/0253673 A1 | 9/2014 | Barredo |
| 2015/0248793 A1 | 9/2015 | Abovitz et al. |
| 2015/0287330 A1 | 10/2015 | Kron et al. |
| 2015/0346813 A1 | 12/2015 | Vargas et al. |
| 2016/0030021 A1* | 2/2016 | Pasternak .............. A61B 10/04 600/424 |
| 2016/0048366 A1 | 2/2016 | Cowin et al. |
| 2016/0179460 A1 | 6/2016 | MacDonald |
| 2017/0042631 A1 | 2/2017 | Doo et al. |
| 2017/0258526 A1* | 9/2017 | Lang .................... H05K 999/99 |
| 2018/0122506 A1 | 5/2018 | Grantcharov et al. |
| 2019/0043238 A1 | 2/2019 | Benishti et al. |
| 2020/0187752 A1 | 6/2020 | Williams |
| 2020/0257485 A1 | 8/2020 | Tsuda et al. |
| 2020/0364862 A1* | 11/2020 | DaCosta ................ G06T 7/564 |
| 2021/0145642 A1* | 5/2021 | Berlin ................ A61M 27/002 |
| 2023/0000498 A1* | 1/2023 | Amiot ................ A61B 17/863 |

FOREIGN PATENT DOCUMENTS

| | | |
|---|---|---|
| WO | 2016/064800 A1 | 4/2016 |
| WO | 2017083768 A1 | 5/2017 |
| WO | 2020/109903 A1 | 6/2020 |

* cited by examiner

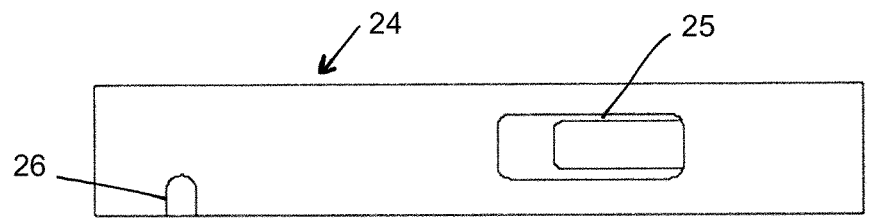
FIG. 4D
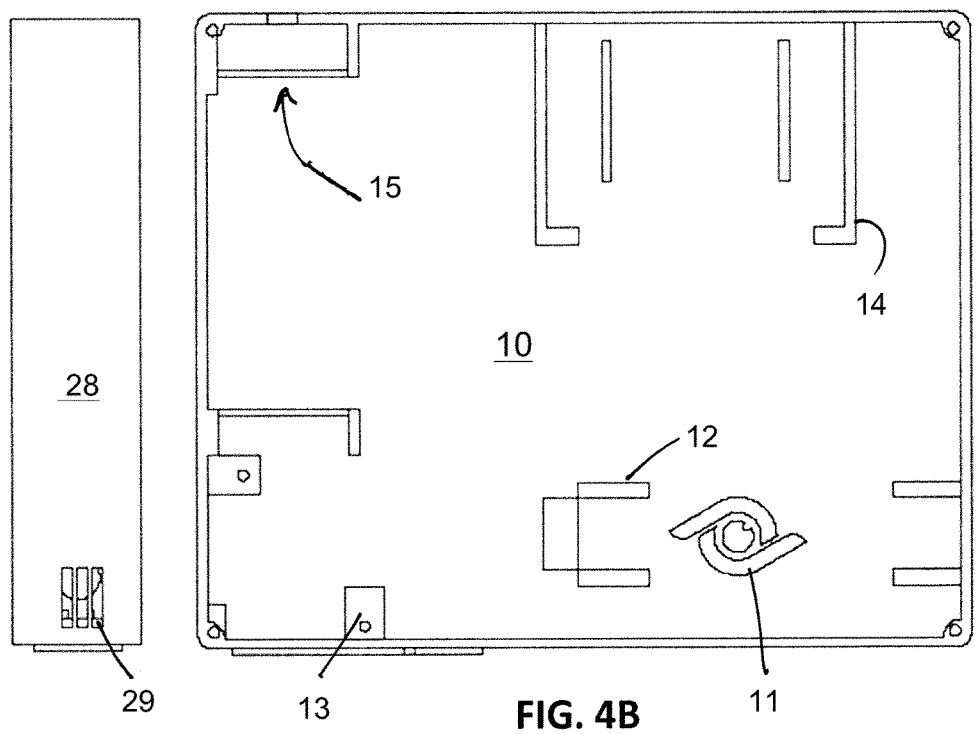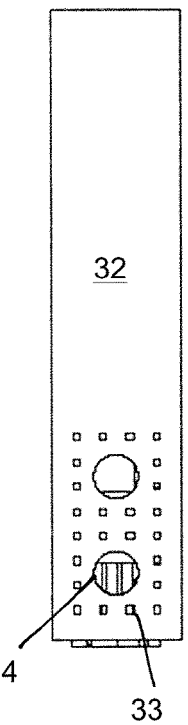
FIG. 4B
FIG. 4E    FIG. 4F
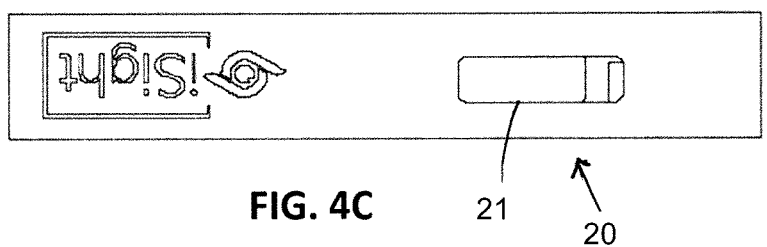
FIG. 4C

AUGMENTED REALITY SURGICAL ASSISTANCE SYSTEM

BACKGROUND OF THE INVENTION

Surgical navigation typically involves surgeons using surgical instruments which are tracked by a navigation system. The position of a tracked instrument in relation to the patient's anatomy is depicted on radiographic images of the patient, thereby allowing the surgeon to use the system to "navigate" the position of the instrument. Many conventional surgical navigation systems utilize a camera (often called a "localizing camera") in the operating room which tracks the positions of surgical tools in three-dimensional space. This positional information is transmitted from the localizing camera to a computer. The computer's monitor displays multi planar, three-dimensional radiographic images of the patient's anatomy relevant to the surgical procedure and which have been uploaded into the computer. The patient's anatomy as positioned in the operating room is "registered" to the radiographic image data using a probe or registration array that is tracked by the localizing camera. The registration array is typically a spaced group of IR reflector elements fixed relative to the patient's anatomy of interest (typically fixed to the skeleton of the patient). In surgical navigation, registration is the process that transforms the three-dimensional radiographic data set (image space) so that it correlates with the three-dimensional coordinates of the corresponding patient anatomy (surgical space), i.e., by the localizing detection of the registration array. The surgical instruments being employed will have their own tracking array with IR reflector elements. Thus, the localizing camera detecting the surgical instrument's tracking array allows the navigation system to project a representation of the surgical instrument on the radiographic image, thus showing the surgeon how the surgical instrument is being oriented relative to the patient's anatomy.

While conventional navigation systems can be effective tools, they have certain drawbacks. First, the computer processing requirements are intensive by necessitating data detected by the localizing camera be converted to instrument positions shown on a radiological image. Because, the required processing capacity is large, the system can be slow in showing a change of instrument position on the radiological image. Second, surgical personnel must be careful not to block the view of the localizing camera or to inadvertently bump the registration array which can de-register the patient's anatomy from the radiological image. Finally, navigation systems require surgeons undergo specialized training in their use and learn through experience the idiosyncrasies of different navigation systems. Third, In a typical navigation system, the surgeon must orient the navigated instrumented tracker facing the camera which limits the orientation at which the instruments can be used as well as add technical difficulties in maintaining the required line of sight in executing the procedure, especially as instruments often have to be reoriented multiple times during each step of the procedure to achieve the desired trajectory.

It would be advantageous to have a system which is more intuitive to use and has faster response times in showing the surgical instruments movement in relation to medical image the instrument is projected onto. It would also be advantageous to have the combined image (i.e., instrument and patient anatomy) displayed in a manner that the surgeon does not need to turn or lift his or her head away from the surgical site in order to observe an operating room (OR) display showing the combined image. Further, it would be advantageous to have a system that completely eliminated the camera, the reference frame, line of sight requirement for the reference frame, line of sight requirement for the instruments and the limitation in angulation at which the instruments can be positioned. Elimination of these aspects of the current systems would significantly reduce the time and difficulty required in using these systems, eliminate errors created by imperfect line of sight of reference frame and instrument trackers as well as add the benefit of minimizing the bulk of the system, therefore creating more functional space in the operating room.

SUMMARY OF SELECTED EMBODIMENTS

One embodiment of the invention is a medical video processing system (MVPS). The system includes a system housing and electronic circuitry within the housing. The electronic circuitry is configured to (a) receive medical video imagery; (b) process the medical video imagery in order to superimpose a virtual medical object (VMO) on the medical video imagery; and (c) transmit the medical video imagery with the VMO in a format that may be received on a wireless display.

Another embodiment is an augmented reality surgical assistance method. The method includes the steps of: (a) capturing a radiological image of a patient's anatomy, together with an instrument guide having a radiolucent portion and a radiopaque portion; (b) computer processing the radiological image to (i) identify boundaries of the instrument guide from the radiological image, (ii) determine a centerline of the instrument guide on the radiological image, and (iii) superimpose on the radiological image a virtual medical object (VMO) extending from a distal end of the instrument guide; and (c) transmitting to and displaying on augmented reality (AR) glasses the radiological image showing the VMO.

BRIEF DESCRIPTION OF THE DRAWINGS

FIG. 4B is the top plate of the controller housing.

FIG. 4C shows the front surface of the controller housing.

FIG. 4D shows the rear surface of the controller housing.

FIG. 4E shows the first side surface of the controller housing.

FIG. 4F shows the second side surface of the controller housing.

DETAILED DESCRIPTION

Figure 1:
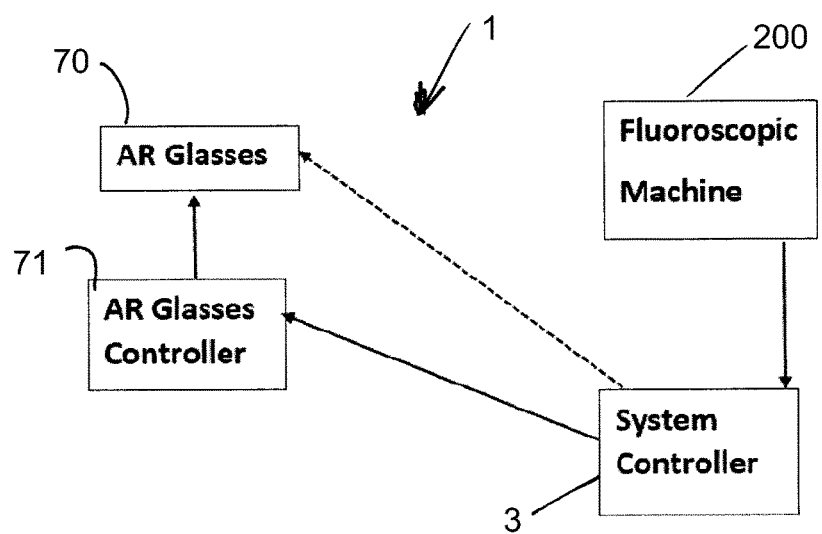
FIG. 1 is a schematic representation of the overall system components.

One aspect of the present invention generally relates to a method and apparatus that superimposes a virtual medical object (VMO) on medical video images. The basic components of one embodiment of such an apparatus is seen in FIG. 1. These components include a system controller 3, augmented reality (AR) glasses 70, and an AR glasses controller 71. A medical video imaging device 200 (in this case a fluoroscopic imaging machine) is shown as the source of medical video images, but imaging device 200 is not a component of this inventive embodiment. Although the medical video imaging device 200 is shown in FIG. 1 as a fluoroscopic imaging machine, any other conventional or future developed source of medical imaging video could be employed, including endoscopy/arthroscopy video imagery, ultra-sound imagery, radiographic imagery (including projection radiography, fluoroscopy and 3-dimensional fluoroscopy), and magnetic resonance imagery. Not all medical imagery need be in the form of video and the invention includes projecting virtual medical objects onto still images.

The controller 3 will receive the medical imagery and through software manipulation, superimpose the VMO on the medical imagery, and then wirelessly transmit the manipulated medical imagery to a display which may be viewed, typically by the surgeon, but in some cases also by other medical personnel. As suggested by FIG. 1, the display may be a pair of AR glasses 70 worn by the surgeon. Some AR glasses 70 will include a separate AR glasses controller 71 (sometimes called the "AR video receiver") which may be worn on the belt of the user with a cable extending to the AR glasses. The AR glasses controller receives and processes the wireless signal from the system controller 3, and sends the image derived from the signal, via the cable, to the projector of the AR glasses. In certain embodiments, the AR glasses controller may be a smart phone running an application allowing it to perform the function of the AR glasses controller. However, there are also AR glasses which have an integral controller allowing the AR glasses to directly receive wireless signals from the system controller 3. At times, the surgeons will utilize the system with the VMO off so that there is no projection and surgeon and other medical personnel can visualize medical images in the AR glasses and benefit from the inherent advantage of positioning the medical images though the AR glasses floating immediately above the anatomy thus eliminating attention shift away from the patient onto another screen positioned away from the patient on the medical device. The wireless aspect of the system along with its portability affords the freedom for the surgeon and medical personnel to position themselves in the ideal orientation in relation to the patient to perform the procedure while maintaining ideal visualization of the medical images. This improves both the comfort and speed of performing the procedure.

Figure 3:
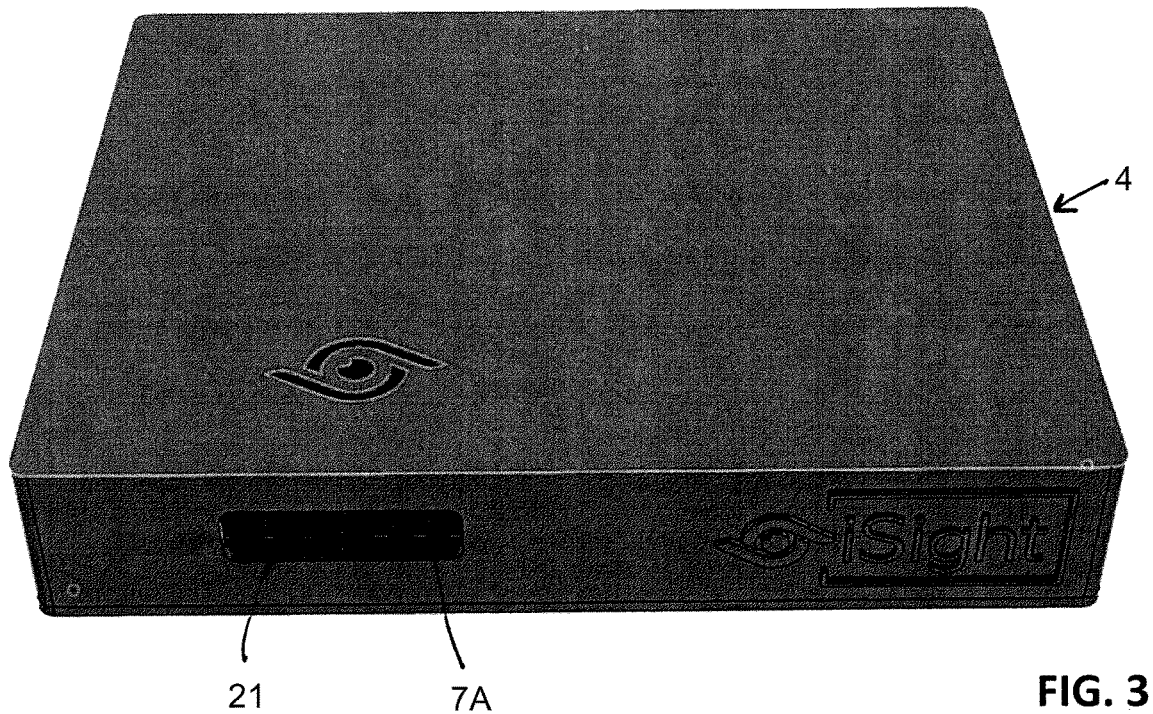
FIG. 3 is a perspective view of the system controller housing.
Figure 4A:
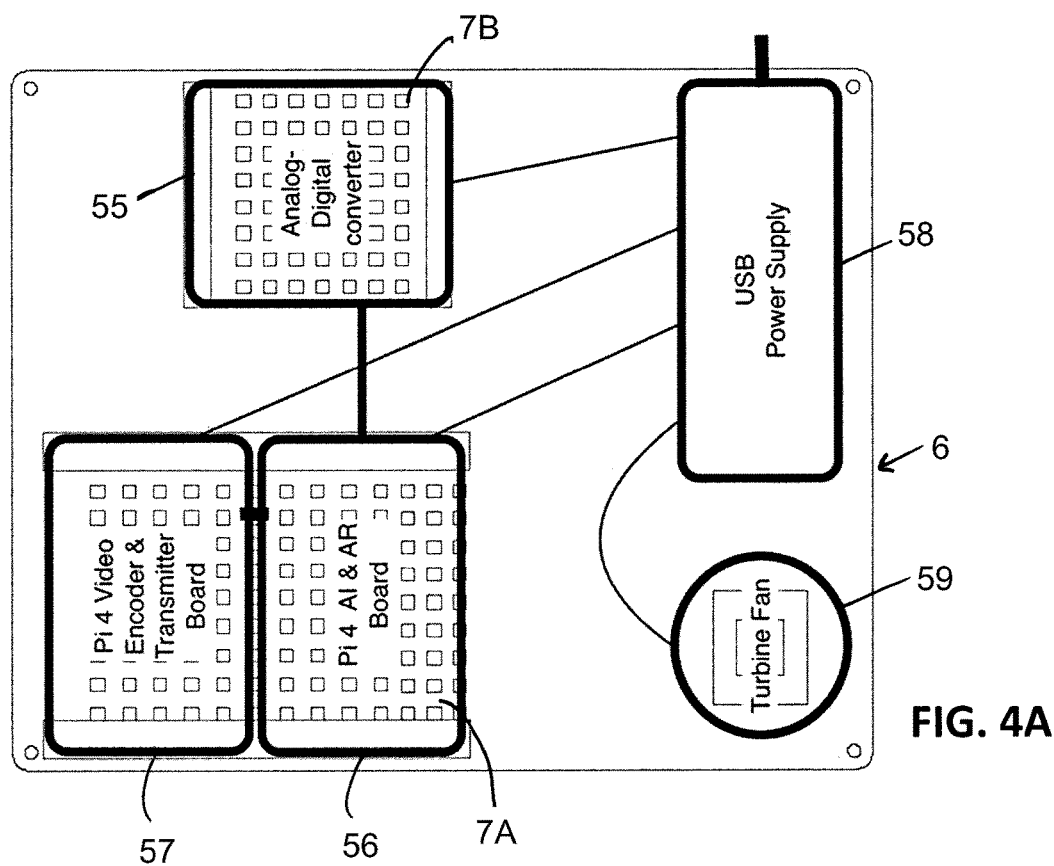
FIG. 4A illustrates major components of the system controller and the bottom plate of the controller housing.

One embodiment of the system controller 3 is seen in FIGS. 3 to 4F. The system controller 3 will have a housing 4 (see FIG. 3) enclosing electronic circuitry which allows the controller 3 to carry out three basic tasks: (i) receive medical video imagery; (ii) process the medical video imagery in order to superimpose a VMO on the medical video imagery; and (iii) transmit the medical video imagery with the VMO in a format that may be received and shown on the display used by the surgeon or other medical personnel. The electronic circuitry in the FIG. 4A embodiment of controller 3 includes the Analog-to-Digital Converter (ADC) 55 which may be an RCa to HDMI converter available from Ablwe of Shenzhen. There is also a video processing system-on-a-chip (SoC) 56 which superimposes the VMO onto the medical imagery video, and a video transmitting SoC 57 which encodes the video with the VMO and transmits it to whatever display device (e.g., AR glasses) which is being employed. In one embodiment, both the video processing SoC 56 and the video transmitting SoC 57 may be Rasberry Pi 4 SoC (aka single board computers) available from the Rasberry Pi Foundation in Cambridge, UK. The controller housing will further include the USB power supply 58 and the fan 59. In one preferred embodiment, fan 59 has an airflow capacity of at least 2.75 CFM, and more preferably over 3.0 CFM. In one example, fan 59 is a 50 mm USB turbine blower available from WINSINN Technology of Shenzhen Weixing Electronic Technology Co., Ltd.

The processing speed of video processing SoC 56 and the video transmitting SoC 57 can be significantly sensitive to increasing temperatures, with higher temperatures resulting in slower processing speeds, which in turn give rise to unacceptable "latency," i.e., the time lapse from capture of the image by a medical video device to presentation of the image on a display viewable by medical personnel. In preferred embodiments, the latency of the system will be maintained under 150 milliseconds (but in other embodiments, the latency could be maintained under 200 milliseconds). Preferred embodiments of the system controller housing will be designed to keep the internal temperature of the housing below about 46° C. in order to maintain acceptable latency speeds. To help maintain this temperature range, the system controller housing will have a number of ventilation windows (or "vent" windows) on the various surfaces of the housing. FIG. 4A suggests how housing bottom surface 6 includes the grilled vent windows 7A and 7B. FIG. 4B illustrates housing top surface 10 includes a vent window 11 in a company logo shape. The inside of top surface 10 further includes a series of mounting brackets for various components, i.e., bracket 12 for video processing SoC 56 and the video transmitting SoC 57, bracket 13 for fan 59, bracket 14 for ADC 55, and bracket 15 for power supply 58. FIG. 4C illustrates front surface 20 with window 21, which serves both as a reading window for a display on video processing SoC 56 and as a vent window. FIG. 4D shows rear surface 24 includes vent window 25 and power code slot 26. FIG. 4E shows first side surface 28 with fan exhaust window 29. FIG. 4F shows second side surface 32 as having grilled vent window 33 and antenna ports 34 (i.e., ports for antennas connected to the video transmitting SoC 57). It can been seen in the illustrated embodiment that the major heat producing electronics will have vent windows (either grills or open windows) facing or adjacent to the component in at least two directions. For example, video processing SoC 56 has vent grill 7A below it and vent window 21 to one side.

Similarly, video transmitting SoC 57 has vent grill 7A below it and vent grill 33 to one side, while vent window 11 faces SoC 56 and SoC 57 from a third direction. ADC 55 has vent grill 7B below it and vent window 25 to its side. A vent window is considered "facing" or "adjacent" a component where no other structure is between the vent window and the component. This controller housing with a large number of vent windows, in combination with fan 59, plays a significant role in keeping the internal housing temperature below about 46° C. while the system controller is in operation. The vents and components are a placed to allow for both passive and active ventilation such that heat can passively and actively be emitted from the system controller.

Figure 5:
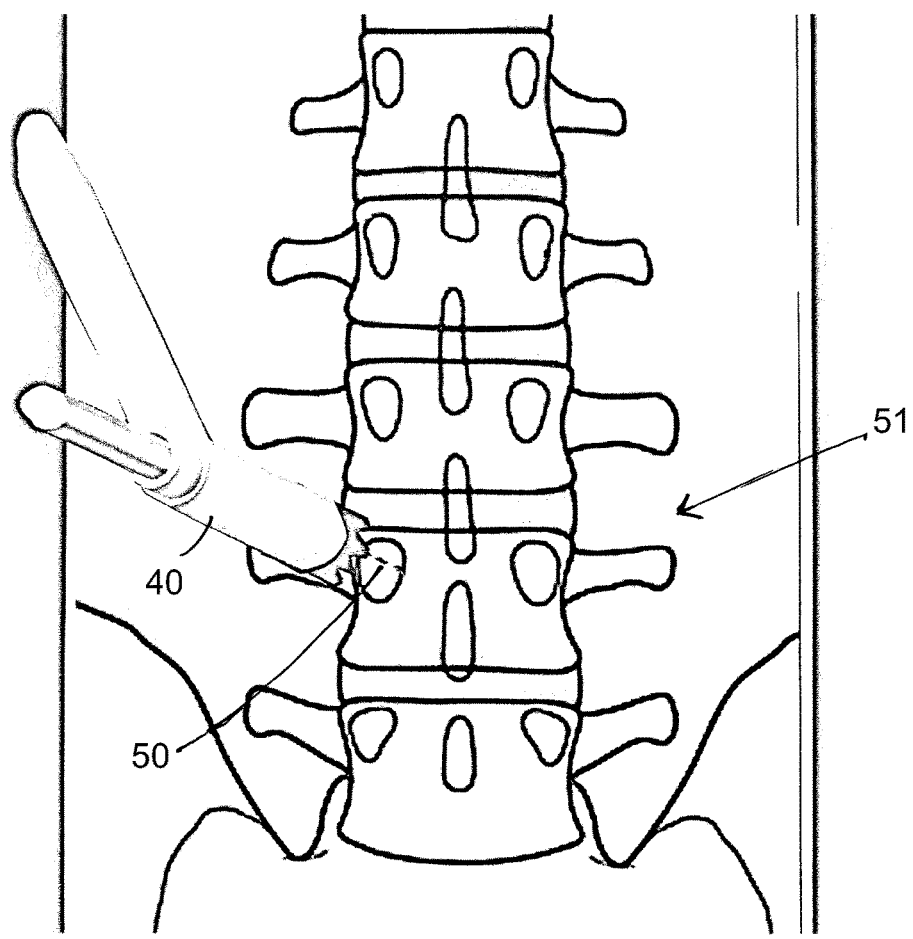
FIG. 5 shows an anteroposterior (AP) view of an instrument guide and spinal column generated by the system for display to a surgeon.

As suggested above, the system controller 3 generally operates to receive medical imagery and through software manipulation, superimpose a virtual medical object (VMO) on the medical imagery, and then wirelessly transmits the enhanced medical imagery to a display. The VMO can be a digital representation of any number of surgical instruments or can be a trajectory line illustrating a particular orientation of a medical instrument. As one example of an image which could be displayed to a surgeon by the present invention, FIG. 5 illustrates a fluoroscopy image AP view of the spine. The instrument guide 40 may be seen faintly in the fluoroscopy image, but is not part of the VMO being superimposed on the fluoroscopy image. The VMO in FIG. 5 is the trajectory line 50 shown to the surgeon in a position so it appears as extending from the end of the instrument guide. The trajectory line 50 is parallel to the longitudinal centerline of the instrument guide, thus the trajectory line illustrates to the surgeon the orientation relative to the spinal image of any surgical instrument (e.g., a drill bit) extending through the instrument guide.

In the upper left hand corner of the image is a projected heart rate and blood pressure as seen by the surgeon (FIG. 5). The surgeon can preoperatively set parameters to alarm for a high or low blood pressure. For example, the surgeon can set to be alarmed when the mean arterial blood pressure (MAP) of the patient is less than 70 mm Hg, indicating that the patient has lost too much blood during the procedure. Alternatively, the surgeon can be set an alarm to be notified when the mean arterial blood pressure is greater than 90 mm Hg, indicating that the patient may be at risk for bleeding because the blood pressure is too high. The display may also include various other real time information (physiological parameters) regarding the patient as typically seen by the anesthesiologist, such as but not limited to, heart rate, respiration rate, and oxygen saturation. The system as outlined below can have another transmitter wirelessly or hardwired connected to an anesthesia machine. The computer processor in the system listed below can image process the numbers as acquired from the anesthesia display and transpose them in the proper position to be seen by the surgeon.

In the upper right corner of the image, the surgeon can see the VMO length as anticipated by the computer and/or set by the surgeon or staff to, for example, 45 millimeters. The length as displayed corresponds to to the projected line as seen on the image and is projected on the fluoroscopy to show how a 45 millimeter screw would appear in the flurosocopic image in that exact plane.

The anesthesia numbers, the VMO length and the projected lines may appear in a color other than black or white so as to distinguish the computer added imagery from the gray scale of the fluoroscopic image.

Figure 7A:
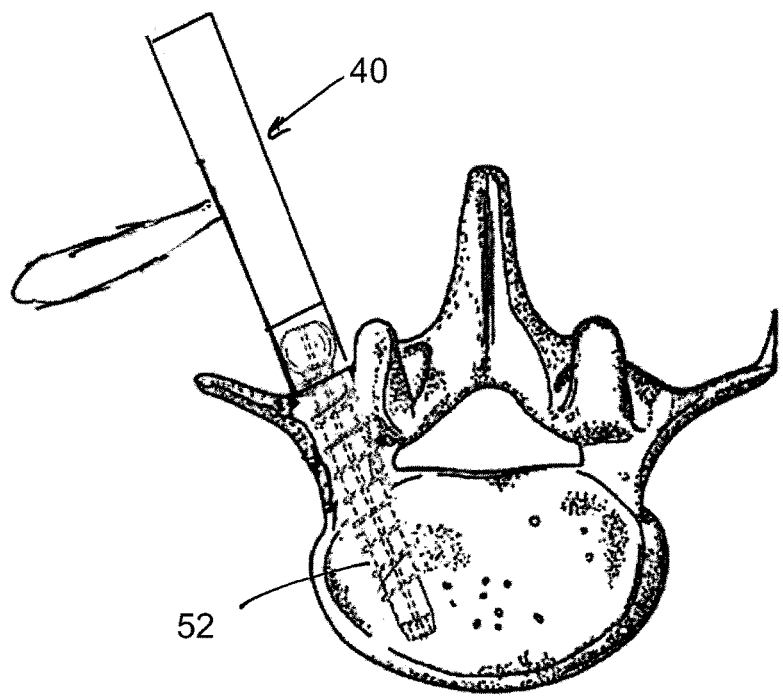
FIG. 7A is a cross-sectional view of a vertebral body showing the instrument guide directing a pedicle screw.
Figure 7B:
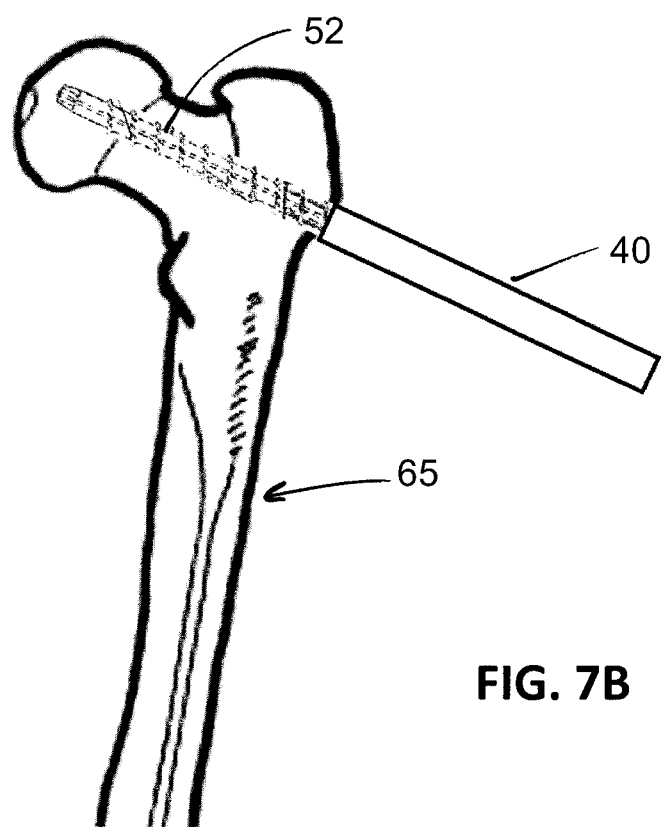
FIG. 7B is a planar view of a femur showing a screw being projected from an instrument guide.

In the FIG. 5 example, the VMO is considered to be the trajectory line itself. However, in other examples not illustrated, the VMO could the digitally created image (i.e., "virtual image") of a medical device, such as a virtual screw, a virtual screw anchor, a virtual suture, a virtual k-wire, or any other type of virtual medical implant. For example, FIG. 7B suggests a medical image of an instrument guide 40 positioned against a femur 65. The system will allow a bone screw 52 of a particular size and length to be superimposed on the medical image at the end of the instrument guide, thereby allowing the surgeon to visualize how the actually placed screw would engage the internal structure of the bone tissue. The system would allow the surgeon to superimpose bone screws of different sizes and lengths in order to best visualize the optimal screw for the specific case at hand. FIG. 7A suggests a virtual screw 52 superimposed on a cross-sectional image (e.g., a CT scan section) of a vertebrae. The instrument guide 40 is positioned against the facet and projecting a virtual pedicle screw onto the image lets the surgeon visualize the screw fully in place and whether the distal end of the screw is in danger of penetrating through to the anterior surface of the vertebral body.

Although not illustrated in the Figures, another embodiment of the invention could superimpose VMOs on ultrasound images/video. Typically, the VMO would be illustrated on the ultrasound image such that it appears to project perpendicularly from the transducer face, i.e., generally in the central direction in which the ultrasound waves are propagating (the transducer face may sometimes be referred to as the "projection plane" of the transducer). This means that when the ultrasound video imagery is received from ultrasonic imaging device and the trajectory image or VMO is projected in a direction such that if observing an image of an anatomic structure in a cross sectional plane (short axis view of a vessel, for example) or longitudinal view (long axis view of a vessel for example), the projected path and/or projected end of the VMO can be visualized. For example, when placing a central line catheter in a jugular vein in the neck, it is important to avoid penetrating the carotid artery. The anatomy of the carotid artery in its relationship to the jugular vein is highly variable from patient to patient and throughout the course of the neck in an individual patient. This system, the augmented reality surgical assistance system (ARSAS), would project a needle path from the starting point on the skin to the plane of the ultrasound transducer in real time such that the physician placing the needle can see the trajectory of the needle prior to placement and actually penetrating the patient's skin. An instrument guide (i.e., needle guide) would be fixed to the transducer such that the system "knows" the position of the needle trajectory relative to the ultrasonic image being generated by the transducer. Thus, the system can superimpose on the ultrasound image a trajectory line (i.e., virtual needle) extending from the position of the needle guide.

Figure 2:
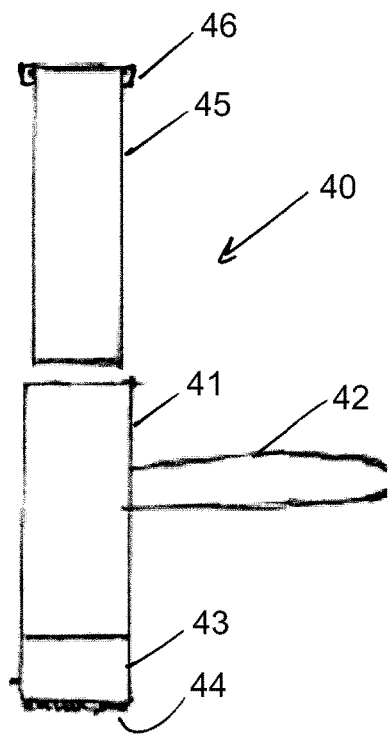
FIG. 2 is one embodiment of a surgical guide used in conjunction with the system.

This virtual needle or VMO, can be projected in the transducer's short axis view or long axis view of the vessel. The ARSAS system will also allow the physician to visualize either the short axis view or long axis view in realtime, while simultaneously visualizing a picture in picture view of the alternative view. For example, if the physician choses to see the long axis view in realtime, the short axis view can appear as snapshot as an active video or as individual image within the picture of the long axis view. If the physician changes the position of the needle, the position of the VMO or virtual needle (VN) will change on the picture in picture view on the short axis as well as the long axis. The VN will appear as the actual needle would appear in the short axis and/or long axis view. The VN will have a distinguishing characteristic, such as a different color or pattern, so that the physician performing the procedure will be able to clearly distinguish the difference between the virtual needle and the actual needle as the latter appears in the ultrasound image. Returning to the FIG. 5 example, the system software will identify the dimensions and orientation of a metal "end cap" on the instrument guide 40 and use that information to calculate the orientation of the trajectory line 50. FIG. 2 illustrates in more detail one embodiment of instrument guide 40 which will include a tubular main guide body 41 to which handle 42 is connected. The main guide body 41 will be formed of a substantially a radiolucent material, e.g., a polymer such as PEEK (polyether ether ketone). A lower portion (or "end cap") 43 of guide body 41 will be formed of a radiopaque material, e.g., a metal such as aluminum or stainless steel. The distal end of guide body 41 (i.e., end cap 43) will include a series of serrations which will help the guide remain in place when pressed against bone or other tissue. Instrument guide 40 will often include one or more smaller diameter tubular guide inserts 45. Guide insert 45 includes the stop collar 46 to limit the travel of insert 45 into guide body 41 and to provide a gripping surface to pull guide insert 45 out of guide body 41. Those skilled in the art will understand that the inner diameter (ID) of guide insert 45 is sized to accommodate one type of surgical instrument (e.g., a bone tap), while the larger ID of guide body 41 is sized to accommodate a larger surgical instrument or object (e.g, a pedicle screw). Although not illustrated, a third guide insert having a diameter smaller than guide insert 45 will often be initially used to guide a drill bit. After the drill bore is created, the third guide insert is removed and the tap is inserted into guide insert 45. After the drill bore is tapped, the guide insert 45 is removed and the screw is guided through the outermost tube formed by guide body 41.

Figure 10A:
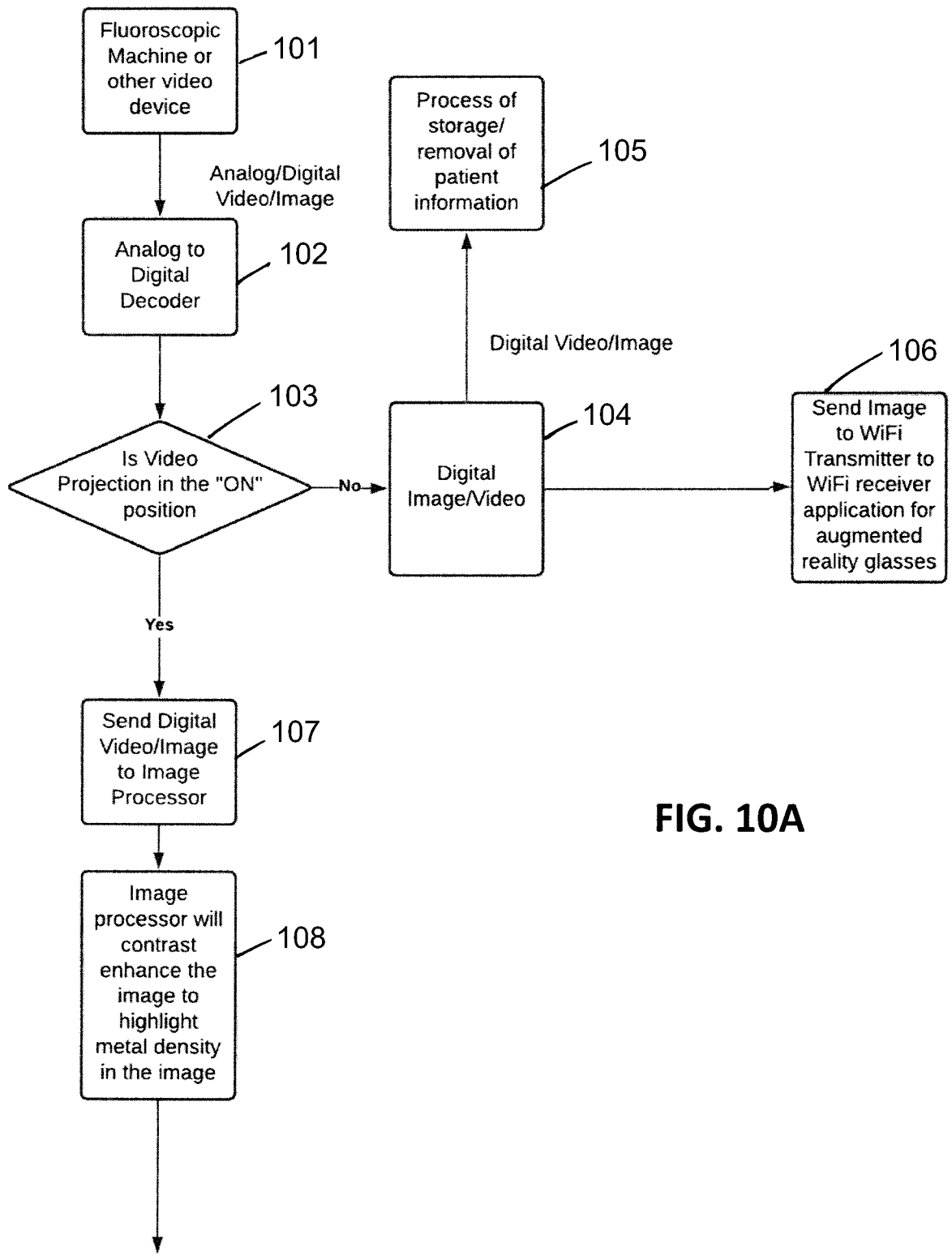
FIGS. 10A and 10B show a flowchart illustrating one embodiment of an image processing algorithm used in the system.
Figure 10B:
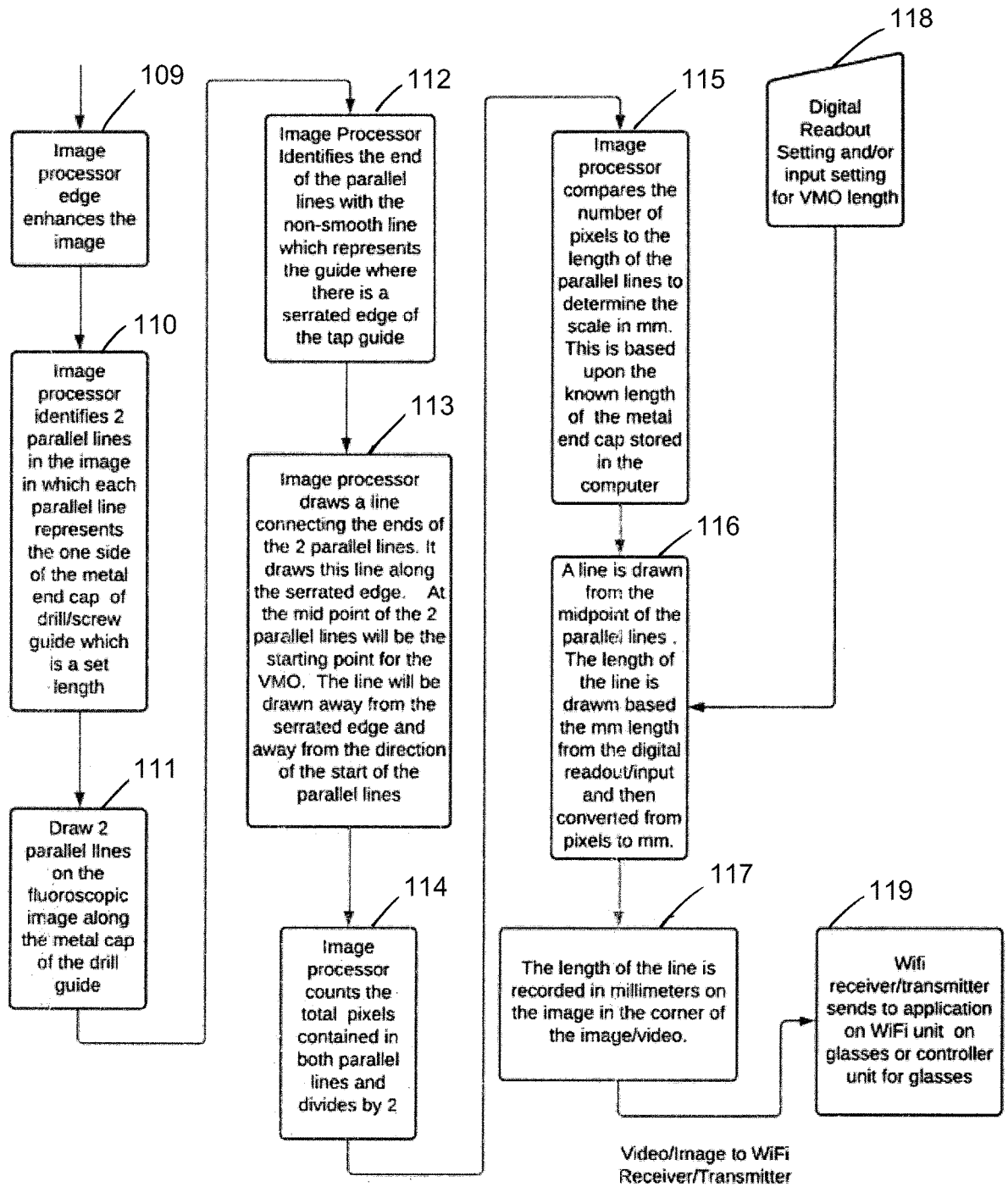

In order to identify instrument guide 40's dimensions and orientation, the system software will generally (i) identify boundaries of the instrument guide's end cap from the radiological image, (ii) determine a centerline of the instrument guide on the radiological image, and (iii) superimpose on the radiological image the trajectory line (or other VMO) extending from a distal end of the instrument guide. FIGS. 10A and 10B suggest a more detailed series of steps the system software will carry out to implement this functionality. In FIG. 10A, step 101, a fluoroscopic machine (or other medical video imaging device) will transmit video/image data to the system controller 3. Typically, the video/image data will be received through a cable, but there could alternatively be a wireless connection between the imaging machine and the controller housing. In step 102, the system controller will employ the ADC 55 to digitize any video data received in analog format. In step 103, the system queries whether the video projection (i.e., VMO superimposition) mode is enabled. If not, the digital video/imagery in step 104 is stored in step 105 and simultaneously transmitted wirelessly to the applicable display system (in this embodiment, the AR glasses of the surgeon).

If the VMO superimposition mode is enabled in step 103, step 107 directs the video/imagery to the video processing SoC 56. In step 108, the system begins the process of identifying the instrument guide by contrast enhancing the image to highlight the metal end cap portion of the instrument guide. In step 109 (FIG. 10B), the edges of this metal end cap are enhanced, while step 110 identifies the two parallel lines which will represent the length of the end cap's edges. In step 111, the video processing SoC creates these two parallel lines on the fluoroscopic image (i.e., on each frame of the video/image). In step 112, the processor identifies the ends of these parallel lines and identifies the "lower" end of these lines by detecting the uneven line caused by the serrated lower edge of the instrument guide metal end cap 43. In step 113, the system constructs a line connecting the two parallel lines along the serrated edge and then identifies the midpoint of a line connecting the two parallel lines from step 112. Step 114 counts the total pixels contained in both parallel lines and divides that number by two. This division by two will provide the average length of the two parallel lines, thereby allowing the length of the projected line (VMO) to be adjusted for the perceived angle of orientation of the end cap, i.e., any perceived difference in length of the two parallel lines. In step 115, the system compares the number of pixels in the parallel lines to the known length of the instrument guide in order to determine the scale of the image (e.g., in millimeters). In essence, this process is identifying the scalar dimensions of the radiopaque portion of the instrument guide by comparing the dimensions detected in the radiological image to a database of scalar dimensions for different instrument guides. The process uses as the boundaries of the instrument guide the two side edges and the bottom edge of the radiopaque portion of the instrument guide. With this information the system calculates a pixels-to-scalar-length-ratio by comparing a known scalar length of at least one side edge of the end cap to a number of pixels forming that side edge in the radiological image. As described above, the pixels-to-scalar-length-ratio may be adjusted for the perceived angle of orientation by adding the number of pixels in the two side edges and dividing by two. Then the selected scalar length of the trajectory line is converted into a number of pixels using the pixels-to-scalar-length-ratio.

Step 116 then generates a trajectory line VMO by superimposing on the image a trajectory line at a midpoint between the parallel lines and extending the trajectory line from the lower end of the parallel lines. The length of the trajectory line has been preselected to be a certain number of millimeters and that preselected length is received at step 118. Using the previously determined pixels-to-scalar-length-ratio, the length of the line in pixels may be determined for the desired (preselected) length of the trajectory line in millimeters. That number of pixels is then employed in creating the trajectory line. In step 117, a line the length of the trajectory line in millimeters is displayed in one corner of the image (see FIG. 5). In step 119, the transmitter SoC encodes and transmits the image with the superimposed VMO to the display device (e.g., the AR glasses). Of note, the surgeon will see the projected VMO at this point. However, typically the parallel lines identification and the pixel counting is done by the image processor and is not seen by or presented on the final image displayed to the surgeon.

It will be understood that the dimensions and other parameters of the VMO are stored in the memory of the system. For example, in the case of an instrument guide, the system only needs to detect the metal end portion and then any other needed dimensions or details of the instrument guide could be retrieved from system memory. It will also be understood that there are different ways a user may pre-set the length of the trajectory line. In one embodiment, a dial on the controller housing could be turned to input the mm length of the trajectory line. In another embodiment, the user may input the trajectory line length by visual activation mechanism incorporated into the system software. For example, many AR glasses also include a camera oriented in the direction of the user's gaze. In such a system, QR codes code be positioned where the surgeon could look at the QR codes which are recorded by the AR glasses camera, which then activates some function in the system (e.g., increase the length of the trajectory line by one millimeter or switch to another VMO, such as a different size pedicle screw). To reduce the chances of an inadvertent visual activation, it would also be possible to place multiple sterilize QR codes on surgical drapes in the sterile field, e.g., three QR codes aligned a few inches apart. When the camera detects all three QR codes, the system takes no action. However, if the surgeon covers the left-most QR code with his hand, the system detects only two QR codes and initiates one type of action. If the surgeon covers the right-most QR code, the system detects a different pair of QR codes and a second type of action is initiated by the system. Obviously, enumerable variations of this concept could be implemented.

Figure 11:
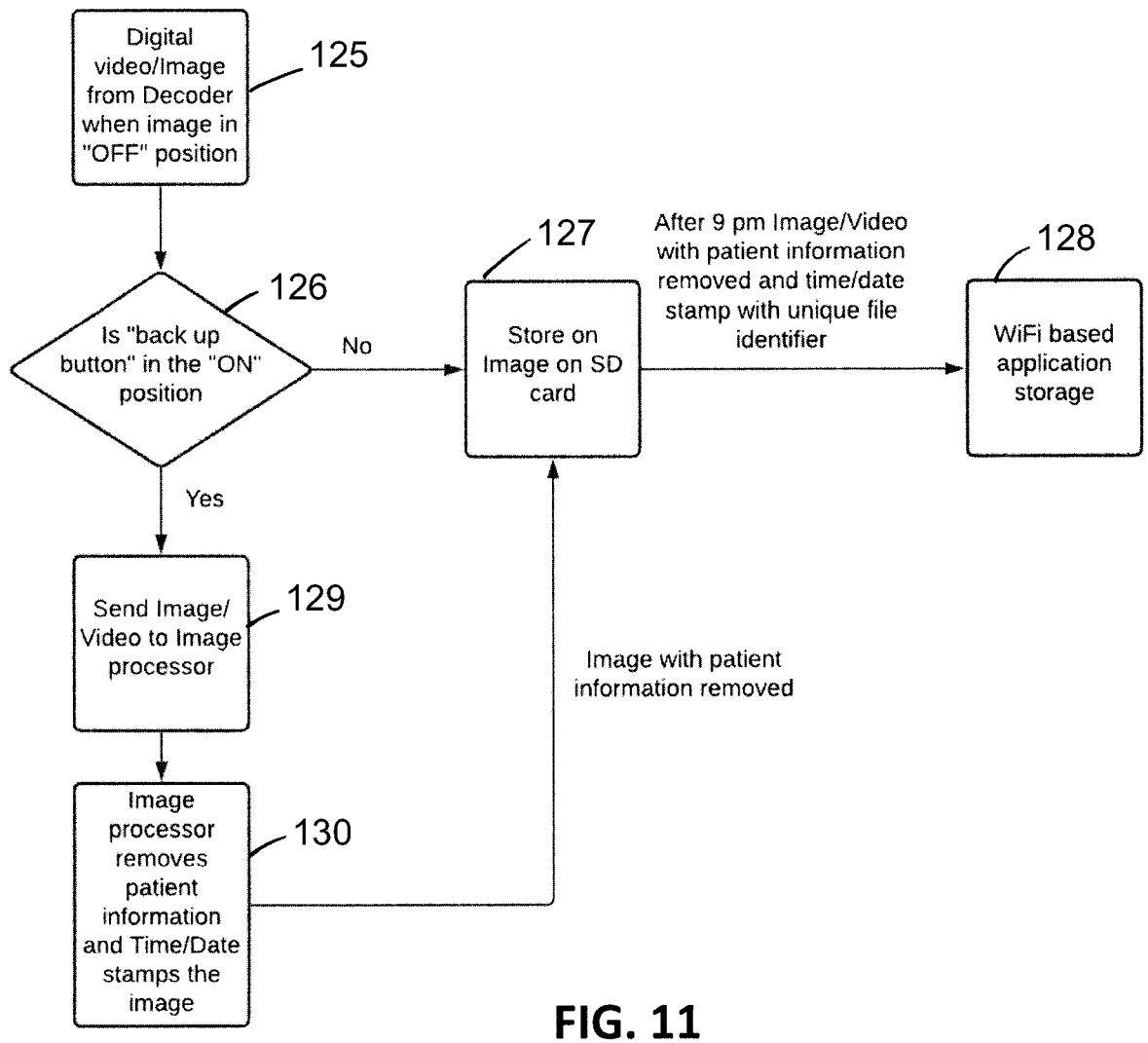
FIG. 11 shows a flowchart of one embodiment of an backup algorithm used in the system.

FIG. 11 illustrates a backup algorithm for the system. Step 125 shows video/image data being received when a VMO is not being superimposed on the video/image data. Step 126 queries whether a video backup selection is enabled. If not, the data is stored on a local (e.g., SD) storage medium in step 127. Alternatively, if the backup selection is enabled, step 129 transmits the data to image processor SoC 56 in step 129. In step 130, any patient information or other protected information is removed from the video/image data and a time/date stamp is added. Then this modified data feed is stored on the local storage in step 127. At a predetermined time during the day, the data which has patient and protection information removed is transferred to an offsite storage location (e.g., an iCloud account) for academic, educational, and/or training purposes.

Figure 6:
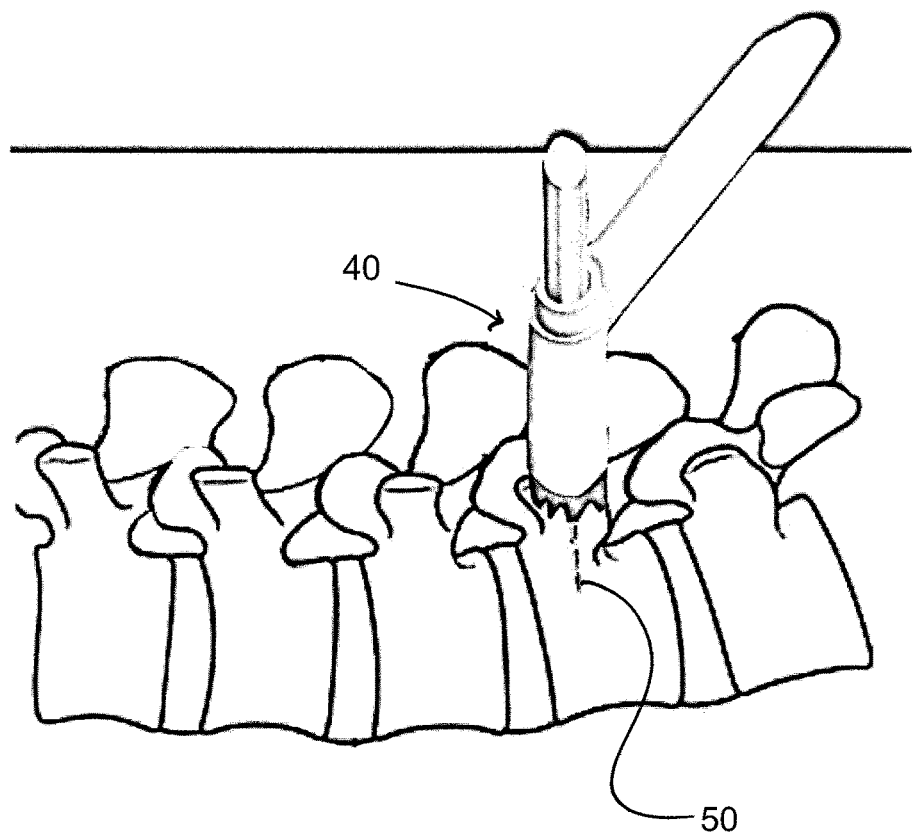
FIG. 6 shows a lateral view of an instrument guide and spinal column generated by the system for display to a surgeon.
Figure 12:
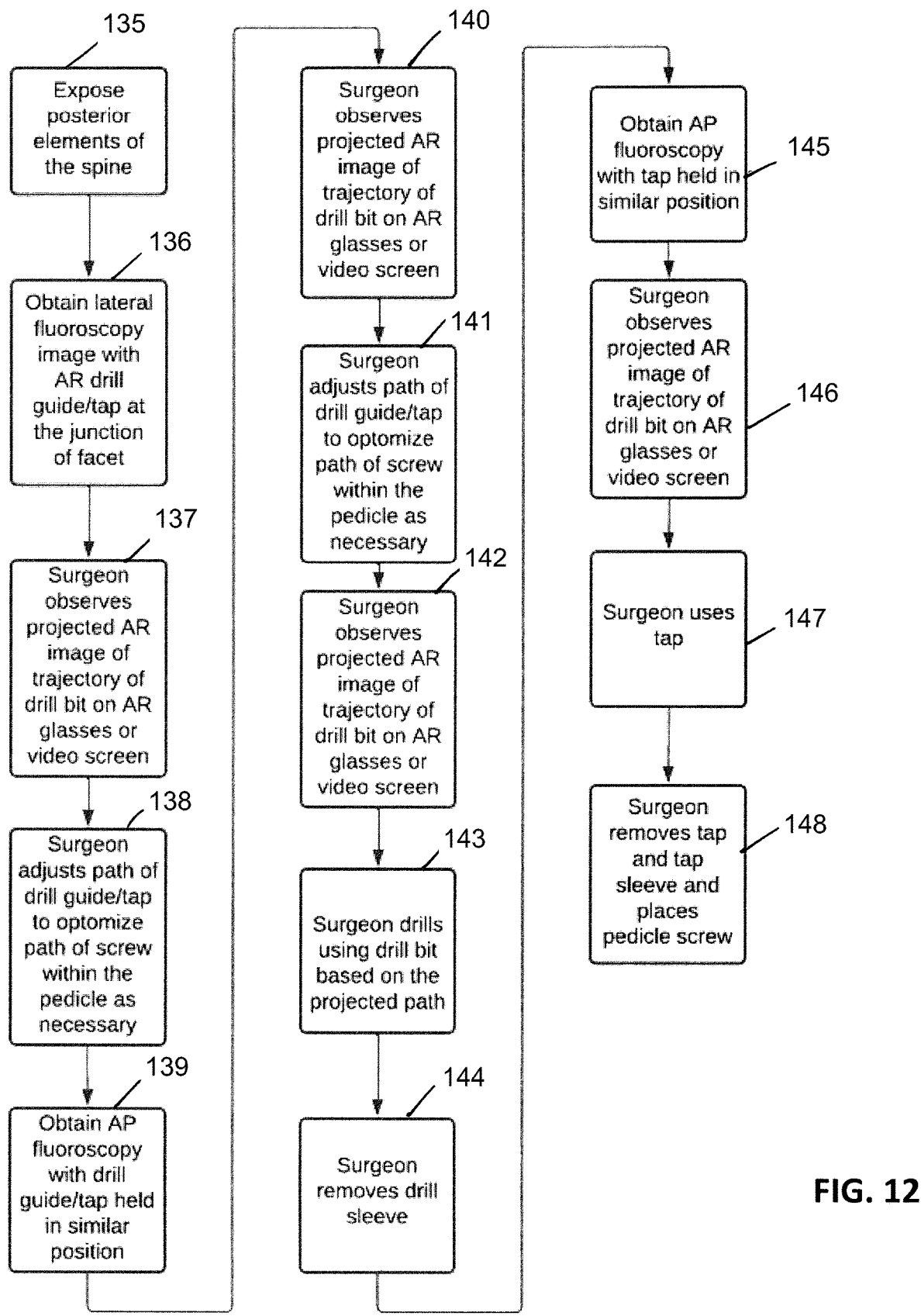
FIG. 12 shows a flowchart of one embodiment of an open surgical procedure using the system.

FIG. 12 suggests one example spinal surgical procedure where the medical video processing system could be employed. Since this is an "open" surgical procedure (as opposed to, for example, a percutaneous procedure), step 135 begins with exposing the elements of the spine being operated upon. In step 136, a lateral fluoroscopy imaging is taken with the instrument guide 40 positioned at the junction of the facet as suggested in FIG. 6. Then in step 137, the surgeon observes the trajectory line 50 seen on the displayed image, which represents, for example, the trajectory of a drill bit being directed by insertion through the instrument guide. Next, the surgeon adjusts the orientation of the instrument guide in order to optimize the anticipated path of the drill bit and ultimately the screw, e.g., a pedicle screw (step 138). Step 139 involves obtaining an AP fluoroscopic image with the instrument guide still being held in place (as suggested in FIG. 5). Again in steps 140 to 142, the surgeon may observe the drill and screw path in the AP perspective as shown with the trajectory line 50 and adjust the orientation of the instrument guide to optimize the screw placement in the vertebrae, an necessary. In step 143, the surgeon inserts the drill bit in the instrument guide and drills the screw bore while observing the trajectory line is maintained in its desired orientation. The surgeon then removes the inner drill sleeve of the instrument guide (step 144) and again observes AP fluoroscopy image in the AR glasses to ensure that the trajectory line 50 is in the proper orientation as the tap is inserted into the instrument guide (step 145 and 146). The surgeon then proceeds to tap the drilled bore hole (step 147) and finally removes the tap and tap sleeve to allow for placement of the pedicle screw (step 148).

Figure 13:
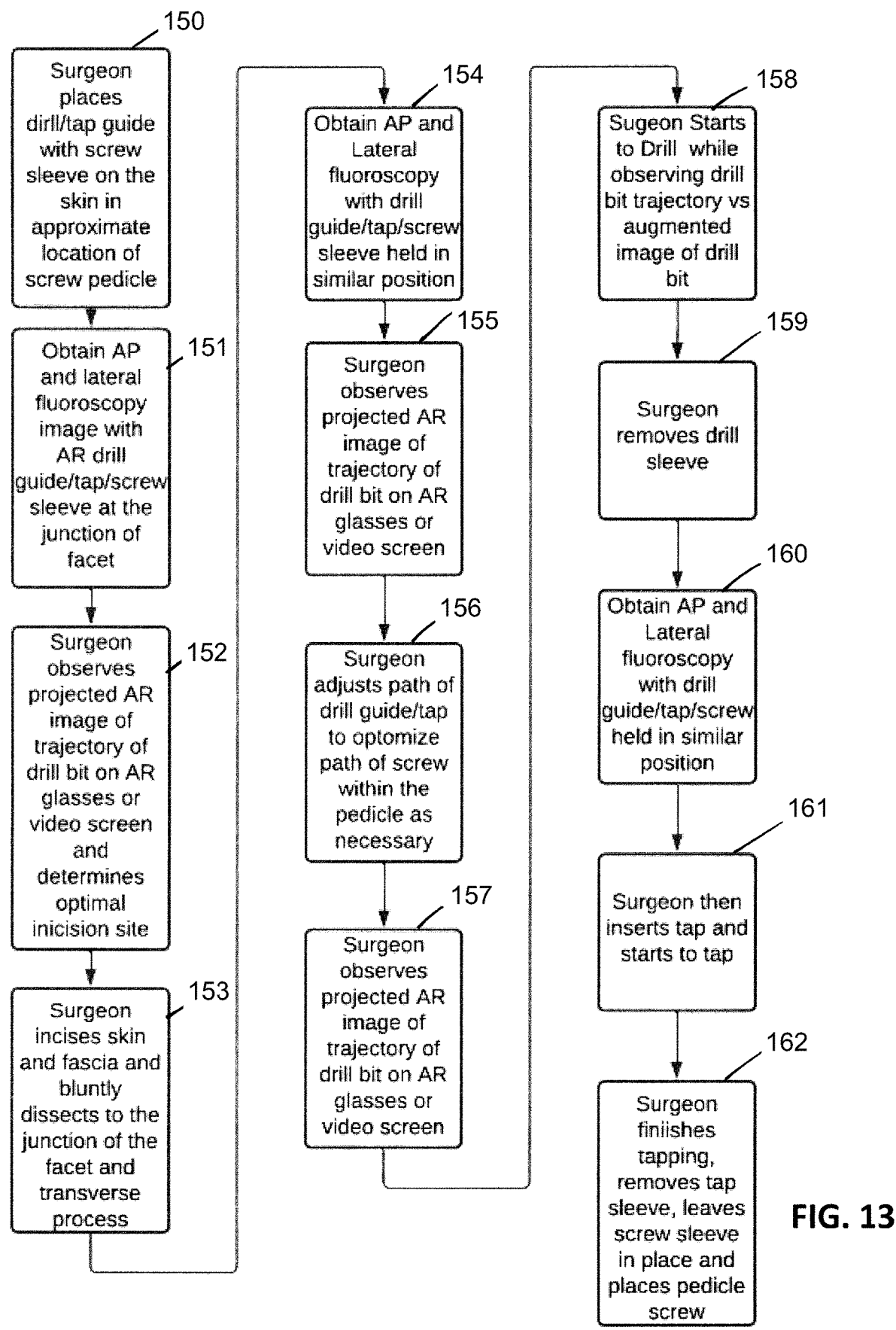
FIG. 13 shows a flowchart of one embodiment of a percutaneous surgical procedure using the system.

A similar percutaneous procedure is suggested in FIG. 13. In step 150, the instrument guide 40 is placed on skin at the estimated location of the pedicle screw placement. AP and lateral fluoroscopic images are obtained showing the trajectory line 50 extending from the instrument guide into the spinal anatomy seen in the fluoroscopic images (step 151). In step 152, the surgeon may observe whether the trajectory line extends through the facet and adjust the position and orientation of the instrument guide accordingly to estimate the optimal incision site, as necessary. In step 153, the surgeon incises the skin and fascia and dissects to the junction of the facet and transverse process. In steps 154-157, the surgeon once again obtains AP and lateral images and observes the location of the trajectory line 50. Then the surgeon adjusts the orientation of the instrument guide 40 in order to judge the optimal screw path. In step 158, the surgeon begins creating the drill bore while observing the drill bit trajectory is overlapping with the trajectory line. After the drill bore is complete, the surgeon removes the drill sleeve from the instrument guide (step 159) and then once again obtains AP and lateral fluoroscopic images to insure the guide is properly aligned for tapping of the drill bore (step 160). The surgeon then taps the drill bore (step 161), removes the tap sleeve, and places the pedicle screw (step 162).

Figure 8:
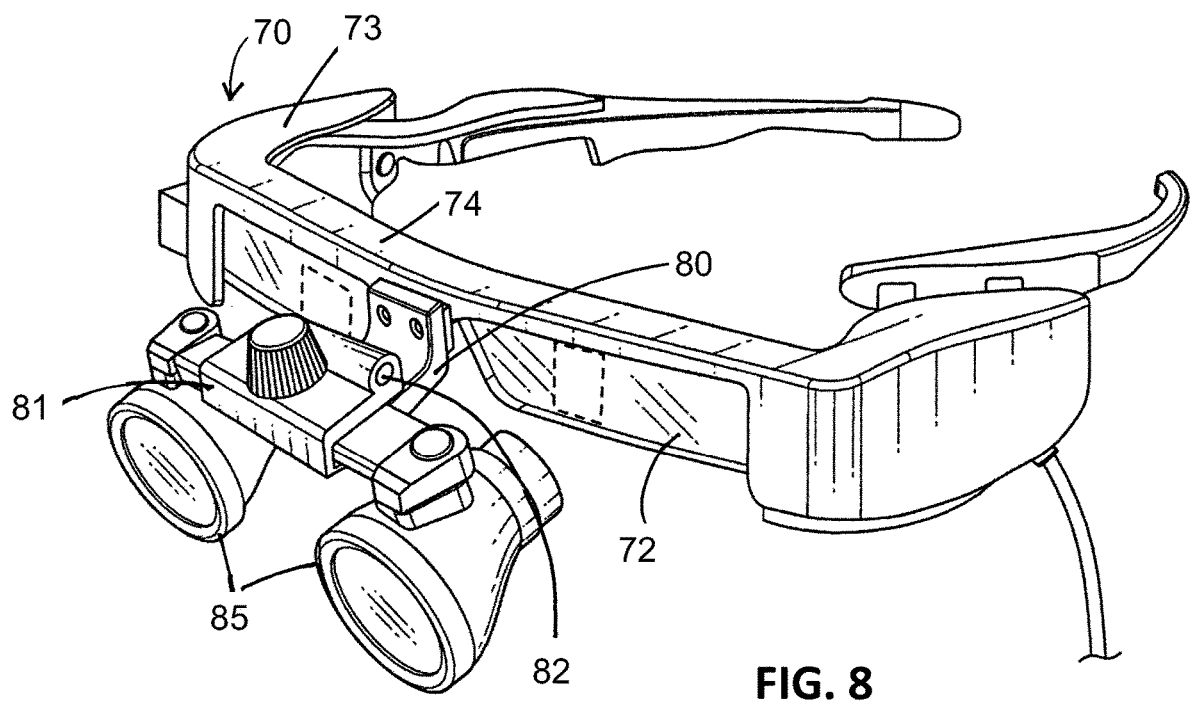
FIG. 8 shows one embodiment of Augmented Reality (AR) glasses incorporating magnifying loupes.
Figure 9C:
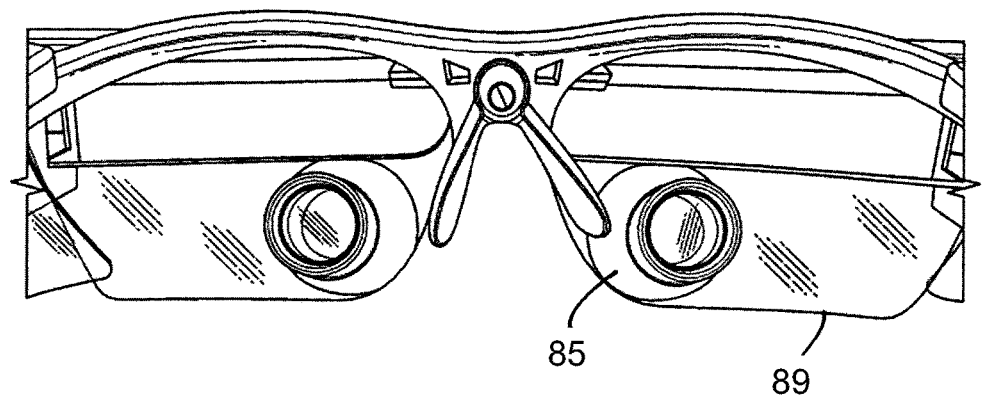
FIG. 9C shows a third embodiment of AR glasses incorporating magnifying loupes.
Figure 9A:
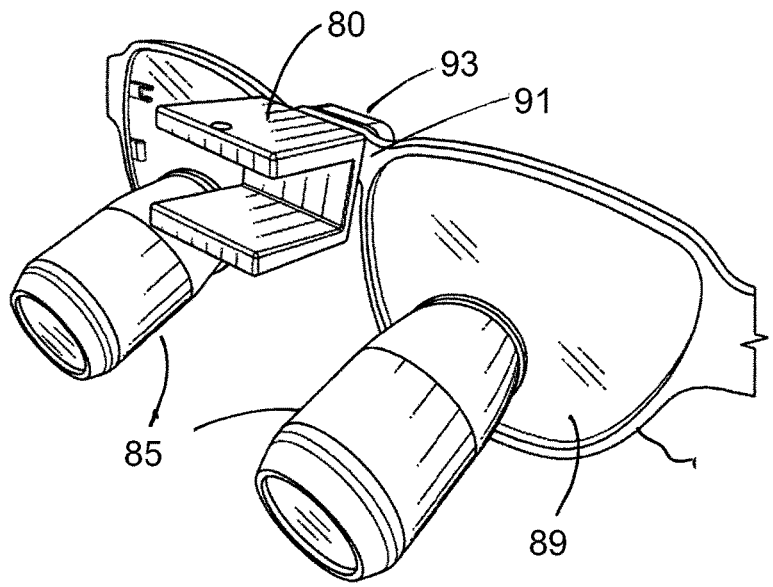
FIG. 9A shows a second embodiment of magnifying loupes configured for attachment to AR glasses.
Figure 9B:
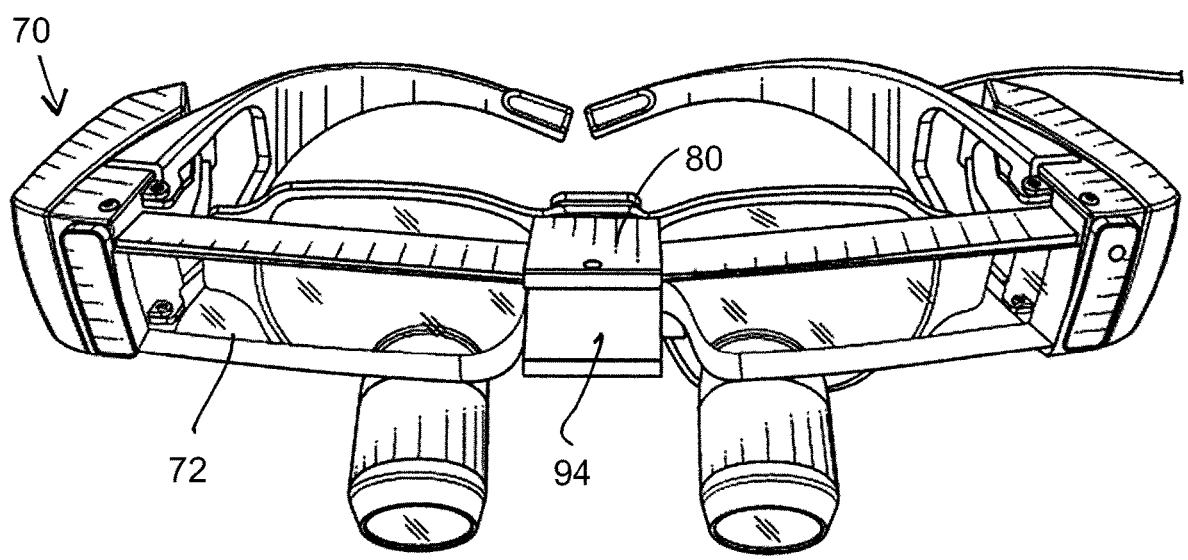
FIG. 9B shows how the FIG. 9A magnifying loupes attach to the AR glasses.

In several embodiments referenced above, the particular display device receiving the modified medical images are augmented reality (AR) glasses, one example of which may be model Moverio BT-300 AR glasses, available from Epson America, Inc. However, a preferred embodiment of the AR glasses will have integrated magnifying loupes such as seen in FIGS. 8 to 9C. Magnifying loupes, or surgical loupes, are typically a pair of magnifying lenses fix on a glasses frame to provide a user with a magnified view of the object being observed. Magnifying loupes generally have a magnification of less than 6×, such as most typically 2.5× to 3.5×, but less commonly including 4.5× and 5.5×. In FIG. 8, the AR glasses 70 generally include the projector units 73 which project the AR images onto display lenses 72. Although not shown in FIG. 8, the AR glasses will have a glasses controller which receives wireless signals and transmits images derived from the signals to the projector units. In FIG. 8, the magnifying loupes 85 are supported by the loupes adjustment bracket 81, which is in turn mounted on the bridge 74 of the AR glasses via the attachment bracket 80. The attachment bracket includes a backing member on the rear (hidden from view) side of AR bridge 74 such that the attachment bracket 80 "clamps" to the AR bridge 74. In this FIG. 8 mounting system, the loupes adjustment bracket 81 is attached to the attachment bracket 80 by pinned connection 82. This allows adjustment bracket 81 to rotate upward to "flip" the loupes 85 upward out of the user's direct line of sight. In FIG. 8, the loupes are positioned below the AR display lenses 72 such that the user can readily switch his or her gaze between the AR display lenses, or looking more downward, through the loupes 85 with only a small movement of the eyes. FIG. 9A shows an alternative manner of combining loupes with AR glasses. In this embodiment, a conventional glasses frame 90 holds conventional lenses 89, and the magnifying loupes 85 are mounted in apertures formed in the conventional lenses (which is itself a conventional manner of mounting magnifying loupes). A C-shaped attachment bracket 80 is fixed to the bridge 91 of the conventional glasses frame 90 by screws (hidden from view) extending through backing member 93, bridge 91, and into attachment bracket 80. As suggested in FIG. 9B, the C-shaped attachment bracket 80 is positioned over the bridge of the AR glasses and firmly grips the bridge of the AR glasses with retaining member 94, which may be secured to attachment bracket 80 with one or more screws. This forms another type of clamp for holding the AR glasses to the loupes. The clamp mechanism allows for fixation of the loupes to the AR glasses without effecting the underlying electronics which may be positioned within the bridge of the AR glasses. Also, this configuration allows for different types and brands of AR glasses to be used with loupes. FIG. 9C shows a slight modification of the FIG. 9B embodiment, wherein the loupes mounting lenses 89 are directly fitted to the AR glasses, i.e., without a separate conventional glasses frame 90.

It will be understood that many embodiments described herein function by identifying a surgical instrument solely based on the medical video imagery. In other words, the current system can function without data from a "secondary sensor" such as the localization camera described in reference to the prior art navigation systems. A secondary sensor could be any device capturing position information regarding the surgical instrument, which is not the primary medical imaging system, i.e., the system which is capturing images of the anatomy of interest.

Although many aspects of the invention have been described in terms of certain specific embodiments illustrated above, many modifications and variations will be obvious to those skilled in the art to which the invention pertains. All such modifications and variations are intended to come within the scope of the following claims. The term "about" as used herein will typically mean a numerical value which is approximate and whose small variation would not significantly affect the practice of the disclosed embodiments. Where a numerical limitation is used, unless indicated otherwise by the context, "about" means the numerical value can vary by +/−5%, +/−10%, or in certain embodiments +/−15%, or possibly as much as +/−20%. Similarly, the term "substantially" will typically mean at least 85% to 99% of the characteristic modified by the term. For example, "substantially all" will mean at least 85%, at least 90%, or at least 95%, etc.

The invention claimed is:

1. An augmented reality surgical assistance method comprising the steps of:
   (a) capturing a radiological image of a patient's anatomy, together with an instrument guide having a radiolucent portion and a radiopaque portion;
   (b) computer processing the radiological image to (i) identify at least one boundary of the instrument guide from the radiological image, (ii) determine a centerline of the instrument guide on the radiological image, and (iii) superimpose on the radiological image a virtual medical object (VMO) extending from a distal end of the instrument guide; and
   (c) transmitting to and displaying on augmented reality (AR) glasses the radiological image showing the VMO.

2. The method of claim 1, wherein the computer processing includes identifying the scalar dimensions of the radiopaque portion of the instrument guide by comparing the radiological image to a database of scalar dimensions for different instrument guides.

3. The method of claim 2, wherein (i) the boundaries of the instrument guide include two side edges and a bottom edge of the radiopaque portion of the instrument guide, and (ii) the computer processing calculates a pixels-to-scalar-length-ratio by comparing a known scalar length of at least one side edge to a number of pixels forming that side edge in the radiological image.

4. The method of claim 3, wherein a selected scalar length of the VMO is converted into a number of pixels using the pixels-to-scalar-length-ratio.

5. The method of claim 4, wherein the pixels-to-scalar-length-ratio is calculated by adding the number of pixels in the two side edges and dividing by two.

6. The method of claim 4, wherein a user inputs the selected scalar length of the VMO.

7. The method of claim 1, wherein the radiological image is video imagery.

8. The method of claim 7, wherein the steps of capturing, computer processing, transmitting, and displaying the video imagery has a latency of less than 150 milliseconds.

9. The method of claim 1, wherein the radiological image is captured with the radiopaque portion of the instrument guide being in contact with a bone structure of the patient.

10. The method of claim 1, wherein the radiological image is a fluoroscopic image, the radiopaque portion of the instrument guide is metal, and the radiolucent portion of the instrument guide is a polymer.

11. The method of claim 1, wherein radiological images are video imagery captured at a rate of at least 50 frames per second.

12. An augmented reality surgical assistance method comprising the steps of:
   (a) capturing a radiological image of a patient's anatomy, together with an instrument guide having a radiolucent portion and a radiopaque portion;
   (b) computer processing the radiological image to (i) identify at least one boundary of the instrument guide from the radiological image, (ii) determine a centerline of the instrument guide on the radiological image, and (iii) superimpose on the radiological image a virtual medical object (VMO) extending from a distal end of the instrument guide; and
   (c) transmitting to and displaying on a wireless display device the radiological image showing the VMO.

* * * * *